(12) United States Patent
Roger

(10) Patent No.: US 6,712,857 B1
(45) Date of Patent: Mar. 30, 2004

(54) ACETABULAR COMPONENT OF TOTAL HIP REPLACEMENT ASSEMBLY

(75) Inventor: Gregory James Roger, New South Wales (AU)

(73) Assignee: Australian Surgical Design and Manufacture Pty Limited, Miranda (AU)

( * ) Notice: Subject to any disclaimer, the term of this patent is extended or adjusted under 35 U.S.C. 154(b) by 53 days.

(21) Appl. No.: 09/926,684
(22) PCT Filed: May 31, 2000
(86) PCT No.: PCT/AU00/00619
§ 371 (c)(1),
(2), (4) Date: Mar. 4, 2002
(87) PCT Pub. No.: WO00/74604
PCT Pub. Date: Dec. 14, 2000

(30) Foreign Application Priority Data

Jun. 2, 1999 (AU) .............................. PQ 0703

(51) Int. Cl.[7] .............................. A61F 2/34; A61F 2/46
(52) U.S. Cl. .................................. 623/22.21; 623/22.39
(58) Field of Search ........................... 623/22.11, 22.15, 623/22.21, 22.22, 22.23, 22.24, 22.39

(56) References Cited

U.S. PATENT DOCUMENTS

| 3,813,699 | A | * | 6/1974 | Giliberty |
| 3,982,281 | A | * | 9/1976 | Giliberty |
| 4,044,403 | A | * | 8/1977 | D'Errico |
| 4,180,873 | A | * | 1/1980 | Fixel |
| 4,666,448 | A | * | 5/1987 | Ganz |
| 4,704,127 | A | * | 11/1987 | Averill et al. |
| 4,715,860 | A | * | 12/1987 | Amstutz et al. |
| 5,009,665 | A | | 4/1991 | Serbousek et al. ............ 623/22 |
| 5,370,698 | A | * | 12/1994 | Heimke et al. |
| 5,725,589 | A | * | 3/1998 | Pfaff et al. |

FOREIGN PATENT DOCUMENTS

| DE | 3414514 A1 | 10/1985 |
| EP | 0142759 A2 | 5/1985 |
| EP | 0262379 A1 | 4/1988 |
| EP | 0613658 A1 | 9/1994 |
| EP | 0888759 A1 | 1/1999 |
| FR | 2630907 | 11/1989 |
| GB | 2159416 A | 12/1985 |
| WO | WO85/02535 | 6/1985 |
| WO | WO97/29698 | 8/1997 |

* cited by examiner

Primary Examiner—Ralph A. Lewis
(74) Attorney, Agent, or Firm—Jacobson Holman PLLC

(57) ABSTRACT

A device for use in surgical procedures involving arthroplasty. The device includes a socket member having a first surface and a second bone engaging surface. The first surface has a bearing surface adapted to receive a counter-component of a joint such as the head of a femur (or prosthesis thereof). The bone engaging surface includes a first, preferably frusto-conical, portion and a second portion preferably including a spherical section.

15 Claims, 3 Drawing Sheets

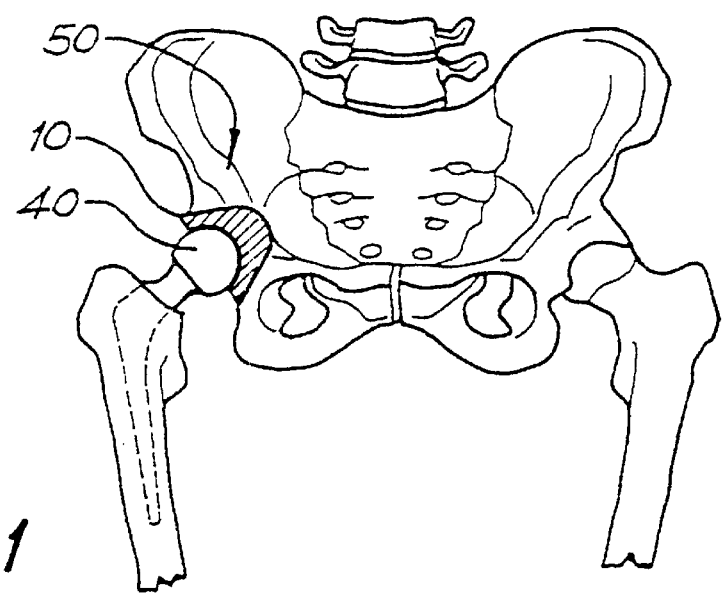
FIG. 1
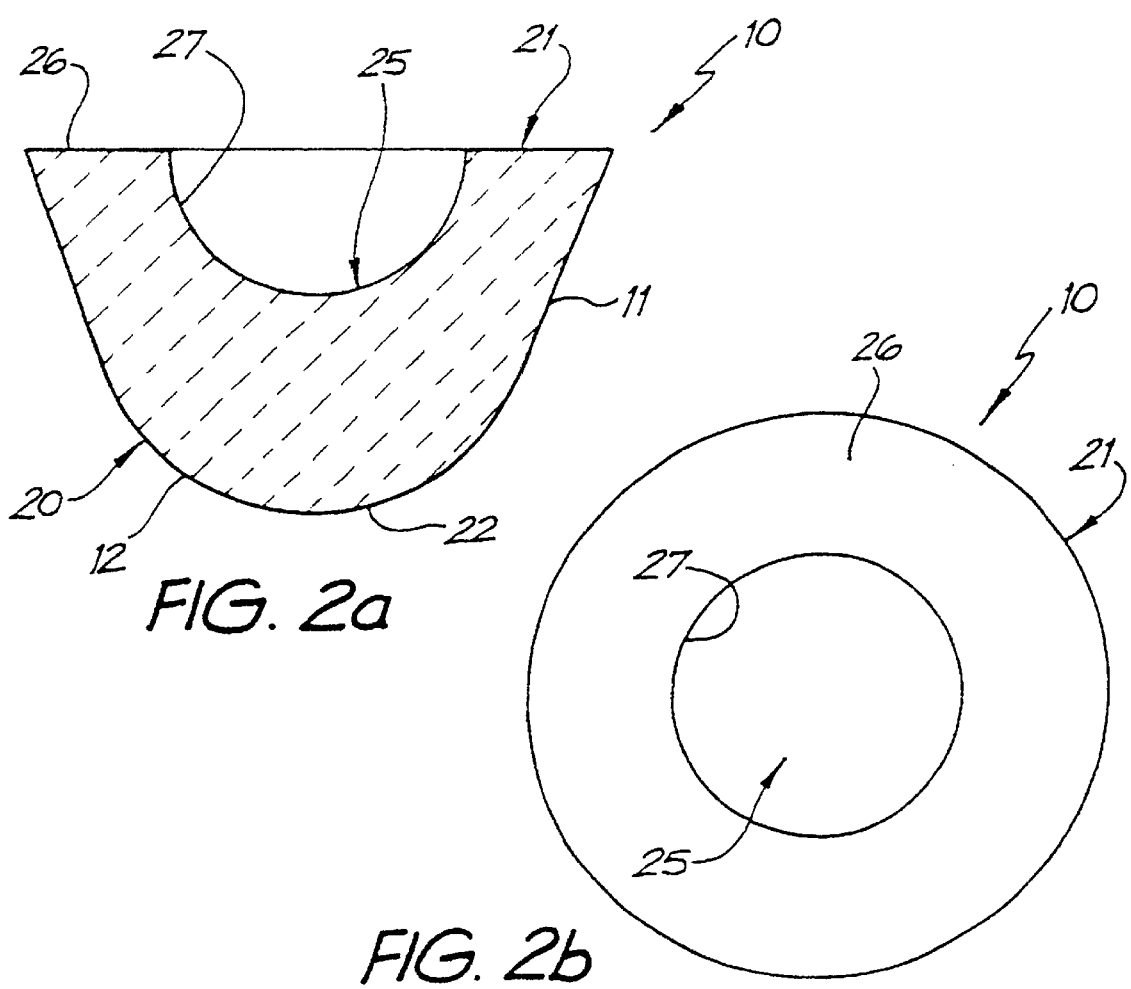
FIG. 2a
FIG. 2b

US 6,712,857 B1

ACETABULAR COMPONENT OF TOTAL HIP REPLACEMENT ASSEMBLY

FIELD OF THE INVENTION

The present invention generally relates to a method and apparatus for use in surgical procedures involving arthroplasty. More specifically, it relates to a prosthetic socket portion of a joint replacement assembly, and a method for its insertion during arthroplasty. Particular reference is drawn to the apparatus in the form of an acetabular portion of a total hip replacement assembly.

BACKGROUND ART

The inclusion of the following description of the prior art is not an admission that the prior art is part of the common general knowledge in Australia.

It is well known to use prosthetic joint replacements in patients with various kinds of disorders affecting the joints, including degenerative disorders, such as severe osteoarthritis.

Over the years, a vast array of materials have been developed and utilised in the construction and manufacture of such prostheses. This is partly because the knowledge base regarding materials, and relevantly biocompatible materials, has been growing. It is also because, despite technological advances, there are a continuing number of complications associated with joint replacement prostheses with which surgeons and patients must grapple. As a result, surgeons and other inventors in the field have had, and are still challenged with, an ongoing quest to improve on the ease of insertion of the prostheses, to reduce the incidence of long and short term complications associated with using them, and to improve on the longevity of both the bio-prosthetic interface, and the prostheses themselves.

Since the present invention refers specifically to a socket portion of a joint replacement assembly, and particularly refers to an acetabular component of a total hip replacement assembly, it is the latter which the following discussion briefly addresses.

The hip joint is comprised of the head of the femur articulating with the acetabulum. The acetabulum is generally cotyloidal in shape, and is often referred to as a "cup".

One of the first designs for the acetabular component of the hip joint, which was developed around 1960, was a hemisphere of metal internally lined with a plastics hemisphere, with the latter acting as the articulation surface. The metal was cemented into the bone and the liner was either pressed into the metal cup during the arthroplasty procedure, or was incorporated into the prosthesis during manufacture. In some later designs, the preferred method of securing the prosthesis was to screw it to the bone. However, while providing good fixation, screws have been found to lead to serious complications in the hip and are now not well regarded. Consequently, some of the more recent developments in acetabular prostheses have focused oil new designs for their bone contacting surfaces. For example, some acetabular prostheses have been manufactured with a self-cutting thread on their bone contacting surface, while others have relied on press fitting along with cement, or a combination of surface roughening and hydroxyapatite.

In addition to considerable variation in the designs of the outer, or bone contacting, surfaces of acetabular prostheses, however, much research has been done in order to provide improved means of engaging the head of the femur (or prosthesis thereof). Forte (U.S. Pat. No. 5,062,853), for example, describes a particular construction for the inner aspect of the acetabular prosthesis which is particularly well adapted to receive and engage a corresponding prosthetic head of a femur.

Nevertheless, while prosthetic hip joint replacements have been shown to be incredibly beneficial for patients who require them, there are still a number of problems associated with their insertion for which further developments in the method and apparatus would be advantageous. The present invention is, most specifically, aimed at improving the bone contacting surface of acetabular prostheses, and therefore addresses many of the problems raised above.

DESCRIPTION OF THE INVENTION

In a first aspect, the present invention consists in a device for use in surgical procedures involving arthroplasty, the device including a socket member having a first surface and a second bone engaging surface, the first surface including at least a bearing surface adapted to receive a counter-component of a joint, and the bone engaging surface including a first portion having a shape, and at least a second portion having a different shape to that of the first portion.

In a second aspect, the present invention consists in a method of inserting a device according to the first aspect during an arthroplasty procedure, the method including the steps of:

a) bringing a surface of an appropriate joint orientation determining means into apposition with the exposed surface of the socket portion of a joint;

b) manipulating the joint orientation determining means so that the correct angular orientation for a socket portion of a joint replacement assembly is determined;

c) forming a hole into the bone adjacent the joint orientation determining means with a hole forming means, using said joint orientation determining means as a guide;

d) removing the joint orientation determining means from apposition with said exposed surface:

e) using the hole formed in step (c) as a guide, reaming an appropriately shaped and sized portion of bone from the bone forming the socket portion of the joint to a desired depth, thereby creating a reamed surface of bone;

f) bringing the bone engaging surface of a device according to the first aspect of the invention into contact with the reamed surface of bone; and g) securing the device to the bone.

The device according to this invention may be used in a range of arthroplasty procedures, but is of particular applicability when used as a replacement for the acetabular component of a hip joint. By virtue of the nature of its function, preferred embodiments disclose that the socket member, as a whole, has a cotyloidal configuration with a longitudinal axis. The first surface of the socket member includes a bearing surface having a radius of curvature which is adapted to receive the counter-component of a joint, such as the head of the femur (or prosthesis thereof) in a hip joint. The socket member is, according to this invention, defined by a bone engaging surface. In accordance with its name, the bone engaging surface is adapted to engage a bony surface comprising a portion of the joint which the device is intended to replace, such as the acetabulum in a hip joint.

Preferred embodiments of the invention disclose that the bone engaging surface of the socket member comprises at least a first and a second portion. In such embodiments, the first portion extends away from a circumferential join with the first surface of the socket member, and the second portion extends away from a circumferential join with the first portion to an extremity.

In further preferred embodiments, as the first portion extends away from its join with the first surface of the socket member, its cross-sectional diameter may decrease at a first rate. In such embodiments, the rate of change in cross-sectional diameter may be linear such that the first portion has a frusto-conical shape. In alternative embodiments, the rate of change may be logarithmic, exponential or may follow any other mathematical expression. In yet further alternative embodiments, the rate of change may itself change from one to another of these mathematical expressions as the first portion extends away from its join with the first surface.

Similarly, as the second portion extends away from its join with the first portion, its cross-sectional diameter may decrease at a second different rate to that of the cross-sectional diameter of the first portion. In preferred embodiments, the rate of change will comply with a mathematical expression which will cause the second portion to form a spherical section, and preferably, a hemi-section or a smaller section still. In alternative embodiments, the discussion of the mathematical expressions according to which the rate of change may comply from the paragraph above is also applicable to the rate of change for the cross-sectional diameter of the second portion.

As indicated above, however, in a preferred embodiment the first portion of the bone engaging surface is frusto-conical, while the second portion comprises a spherical section. Construction of the device according to either of these aspects of the invention, therefore, envisages the bone engaging surface of the socket member including any one of a plurality of combinations of portions having these, and other additional, shapes.

In some such embodiments of the invention, for example, the bone engaging surface includes a plurality of portions of different shapes, wherein at least one portion is frusto-conical, and another, comprises a spherical section, while in other embodiments, the bone engaging surface includes only two portions, each having one of the latter shapes. Indeed, embodiments of the invention wherein these two portions alone comprise the bone engaging surface are preferred. Consequently, the foregoing description outlines preferred structural combinations of the frusto-conical portion and portion comprising a spherical section for the bone engaging surface of the socket member.

In preferred embodiments, the bone engaging surface of the socket member is substantially hemispherical, having its rounded extremity formed by the portion of the bone engaging surface comprising a spherical section. In other words, in these particular embodiments, the frusto-conical portion of the bone engaging surface is oriented so that its smallest cross-sectional diameter meets, circumferentially, with the hemisphere formed by the portion comprising a spherical section; and its largest cross-sectional diameter meets, circumferentially, with the first surface of the socket member.

In alternative embodiments, the bone engaging surface comprises a frusto-conical portion, a portion comprising a spherical section, and a planar portion or a portion comprising a section of a larger sphere than the latter. Such embodiments disclose a similar configuration to that described in the preceding paragraphs. However, while the extremity of the bone engaging surface still has a substantially hemispherical surface, a portion of that surface is essentially planar.

As indicated earlier, the scope of this invention is not limited to the embodiments just described. There are multiple variations for the construction of the bone engaging surface having a plurality of portions, each with unique shapes, which fall within its scope. However, it is noteworthy that the incorporation of a bone engaging surface having a combination of a frusto-conical portion and portion comprising a spherical section may contribute considerably to the functionality and securability of the socket member.

In replacing a socket portion of a joint, the fixation of the socket member must be able to withstand rotational and other movement influencing forces created during articulation of the joint. While the means used to secure the socket member to the bone (see below) will be of substantial importance in this regard, having a frusto-conical shape for a portion of the bone engaging surface of the invention is also of particular value, as such a shape has excellent side rotational stabilising capacity.

In addition, such a shape helps to ensure that any compressive forces which the socket member applies to the bone during, for example, weight-bearing, is desirably distributed: with a frusto-conical shape, compression of the bone will be greatest at the largest cross-sectional diameter of the frusto-conical portion, namely, around the first surface of the socket member. The latter will, when the socket member has been inserted according to this invention, be located near the surface of the bone. It is desirable for the greatest compressive force which the socket member applies to the bone to be distributed at this location. This is because, if the greatest compression occurs in deeper regions of the bone, for example, those regions adjacent the extremity of the bone engaging surface of the socket member, then the surface bone is protected from stress and tends to weaken.

The capacity of a socket member according to this invention to distribute such compressive forces desirably is further augmented by the presence of a portion comprising a spherical section near or at the extremity of the bone engaging surface. In preferred embodiments, the bone engaging surface of the socket member, despite being comprised of a plurality of portions each having unique shapes, is continuous, in that the meeting loci of these portions are not interrupted, or constructed, by a sharp edge or a 'step'. When the portion comprising a spherical section is at the extremity of the bone engaging surface it acts as a further means to ensure that no such edge or step is in contact with the surrounding bone. The value of ensuring as much, especially near the extremity of the bone engaging surface, is that an edge-like or step-like protrusion would, during the application of weight-bearing compressive forces, act as a stress riser on the bone. For the reasons already outlined, among others, this is not desirable.

Preferred embodiments also disclose that a bearing surface is located at the first surface of the socket member. Such a bearing surface, has the capacity to receive the counter-component of a joint such as the head of the femur (or prosthesis thereof) in a hip joint.

In some such embodiments of the invention, the first surface of the socket member is comprised of a relatively planar surface into which the bearing surface forms an indent. Because the bearing surface receives the counter-component of the joint, the materials used in the construction of the invention warrant discussion: while there are no particular limitations on the materials to be used in the manufacture of the socket member, it is replacing a bony component of a joint, and must, therefore, have similar characteristics in terms of strength and resilience. Various metals, as well as ceramics, or carbon fibre may all be appropriate. As an integral component of the socket member, the bearing surface will also be made of such a material. However, since this surface of the socket member represents the articulating surface of the joint, it is desirable to use a high-wear resistance material such as polyethylene or ceramics. Accordingly, in preferred embodiments of the invention, a shell being made of polyethylene, or similar appropriate material, and having a shape which corresponds with the bearing surface is machine fitted to the latter. Note, however, that although machine fitting provides for a tighter fit and a convenient form of manufacture, it is not a requisite component of this invention that the shell be fitted by machine. Indeed, any appropriate method of fitting the shell, including for example, by known methods of clipping it into position, falls within the scope of this invention.

It is further noteworthy that as the bearing surface comes under load, there may be relative movement, or micro-motion, between the shell and the bearing surface of the socket member to which it is fitted. This can generate wear particles. In order to render less likely such generation, preferred embodiments of the invention disclose that an interface between the bearing surface of the socket member and the shell is surface-coated with a material, such as titanium nitrate or titanium carbide.

Additionally disclosed is a method for inserting a socket member according to the invention during an arthroplasty procedure. Although not required in many cases, it may initially be necessary for the surgeon to perform a small hemispherical ream into the bone forming the socket portion of the joint. It may be appropriate to do so in cases where this part of the joint has undergone severe pathological degeneration. Nevertheless, whether or not the decision is made to perform the small hemispherical ream, the method generally includes the steps of:

a) bringing a surface of an appropriate joint orientation determining means into apposition with the exposed surface of the socket portion of the joint. For the purposes of this disclosure, a "joint orientation determining means" refers to an appropriate device which can be used to determine the correct orientation for a replacement prosthesis;

b) manipulating the joint orientation determining means so that the correct angular orientation for a socket portion of a joint replacement assembly is determined. Such determination is critical, both for ensuring the best alignment and also for finding a position which provides the least likelihood of dislocation. Determination of the correct angular orientation may be achieved by having reference to appropriate anatomical landmarks, by simple visualisation, or with whatever method is preferred by the surgeon;

c) forming a hole into the bone adjacent the joint orientation determining means with a hole forming means, such as a drill bit, using said joint orientation determining means as a guide. In preferred embodiments of the invention, the joint orientation determining means is pre-prepared with a hole designed to receive the hole forming means. In alternative embodiments, it may not be;

d) removing the joint orientation determining leans from apposition with the exposed surface of bone;

e) using the hole formed in (c) as a guide, reaming an appropriately shaped and sized portion of bone from the bone forming the socket portion of the joint to a desired depth, thereby creating a reamed surface of bone. In preferred embodiments, the reamed surface should extend to a depth slightly beyond the depth attained, according to this invention, by the extremity of the bone engaging surface of a fully inserted socket member.

f) bringing the bone engaging surface of a socket member according to the invention into contact with the reamed surface of bone; and g) securing the socket member to the bone. In preferred embodiments, the socket member is press fit, and not threaded. While a socket member having a thread is not outside the scope of this invention, the press fit solution is preferred as it significantly decreases the technical complexity of insertion. As explained in (e) above, when the socket member is fully inserted, preferred embodiments disclose that there should be a small space between the extremity of the bone engaging surface and the reamed surface of bone. This space provides room to allow for a small amount of subsidence of the socket member when it is subjected to compressive forces, for example, during weight-bearing.

Reinforced fixation of the socket member in the correct position may additionally be achieved by cement, by a combination of roughening and hydroxyapatite, or by any other appropriate means.

The socket member, according to this invention, is now ready to receive the counter-component of the joint, or a prosthesis thereof.

More specifically, in cases where a socket member according to the invention will be used to replace the acetabular portion of a hip joint, similar commentary regarding the steps above is appropriate, but in summary, the method includes the following:

a) bringing a convex surface of a hemispherical cup (an appropriate joint determining means for hip joint arthroplasty) into apposition with the exposed surface of the acetabulum;

b) manipulating the hemispherical cup so that the correct angular orientation for an acetabular portion of a total hip replacement assembly is determined;

c) forming a hole into the bone adjacent the hemispherical with a hole forming means, such as a drill bit, using said hemispherical cup as a guide;

d) removing the hemispherical cup from apposition with the exposed surface of the acetabulum;

e) using the hole drilled in (c) as a guide, reaming an appropriately sized frusto-conical portion of bone from the acetabulum to a desired depth, thereby creating a reamed surface of bone;

f) bringing a socket member according to this invention into contact with the reamed surface of bone; and g) securing the socket member to the bone.

The socket member is now ready to receive the head of the femur, or a prosthesis thereof.

In accordance with this latter description, pertaining to a method for inserting a device according to the invention in an arthroplasty procedure on the hip joint, a further aspect to the invention is disclosed:

In a third aspect, the present invention consists in a method of inserting a device according to the first aspect during an arthroplasty procedure involving the hip joint, wherein the bone engaging surface is comprised of a first frusto-conical portion and at least a second portion, wherein the second portion includes a spherical section, the method including the steps of:

a) bringing a convex surface of a hemispherical cup into apposition with the exposed surface of the acetabulum;

b) manipulating the hemispherical cup so that the correct angular orientation for an acetabular portion of a hip replacement assembly is determined;

c) forming a hole in the acetabulum with a hole forming means, using the hemispherical cup as a guide;

d) removing the hemispherical cup from apposition with said exposed surface of acetabulum;

e) using the hole drilled in (c) as a guide, reaming an appropriately sized frusto-conical portion of bone from the acetabulum to a desired depth, thereby creating a reamed surface of bone;

f) bringing a device according to this aspect of the invention into contact with the reamed surface of bone; and g) securing the device to the bone.

A significant advantage of the present invention is that in the event that an error is made while carrying out step (e), and the ream is found to be in the wrong direction, the option is still available to then use a hemispherical reamer to slightly enlarge the reamed surface of bone, with minimal extra bone resection. In this instance, it will be possible to still position a hemispherical socket member against the reamed hemispherical surface and secure it to the bone. Thus, the present invention additionally offers a satisfactory avenue for dealing with initial errors of alignment in reaming the appropriately sized frusto-conical portion of bone.

BRIEF DESCRIPTION OF THE DRAWINGS

By way of example, preferred embodiments of the invention are described with reference to the accompanying drawings in which:

FIG. 1 is a schematic representation of a prosthetic total hip replacement assembly, as inserted, following arthroplasty to the right hip;

FIG. 2a is a cross-sectional view of a socket member according to a preferred embodiment of the invention;

FIG. 2b is a diagrammatic representation of a top view of the socket member in FIG. 2a, illustrating the first surface of that socket member;

FIG. 3a is a perspective view of a socket member according to the preferred embodiment of the invention illustrated in FIG. 2a;

FIG. 3b is a cross-sectional view of the socket member of FIG. 3a;

FIG. 4b is a cross-sectional view of the socket member of FIG. 4a;

PREFERRED MODE OF CARRYING OUT THE INVENTION

Figure 3A:
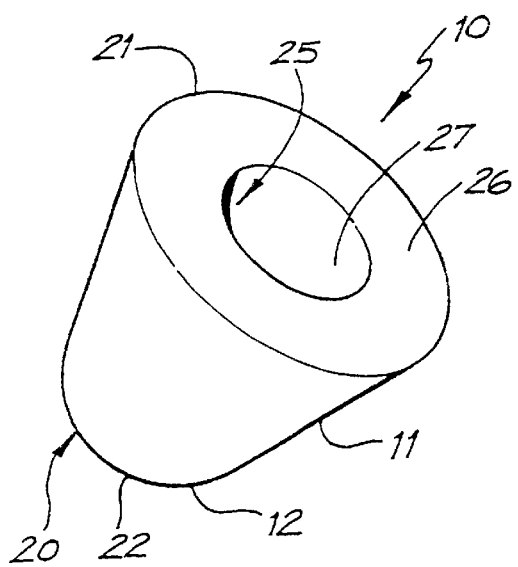
Figure 3B:
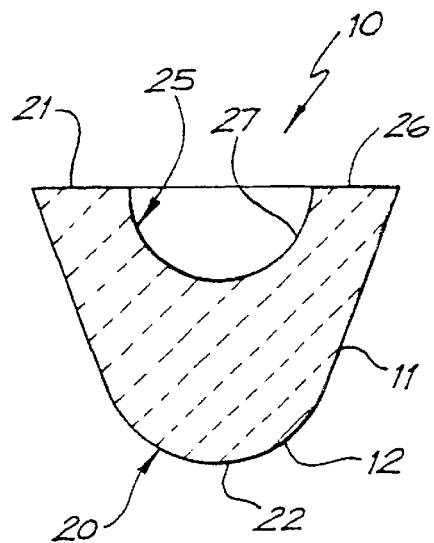
Figure 4A:
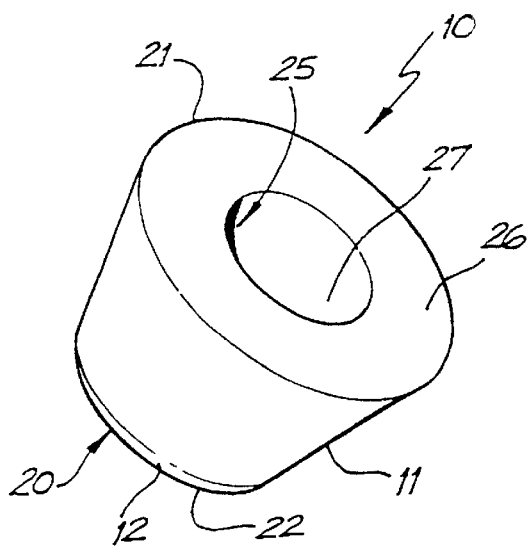
FIG. 4a is a perspective view of a socket member according to another embodiment of this invention.
Figure 4B:
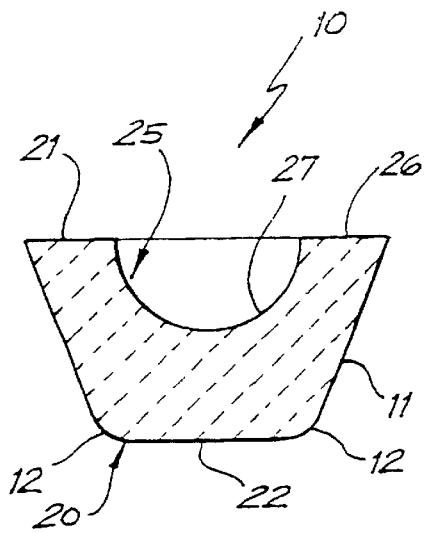
Figure 5A:
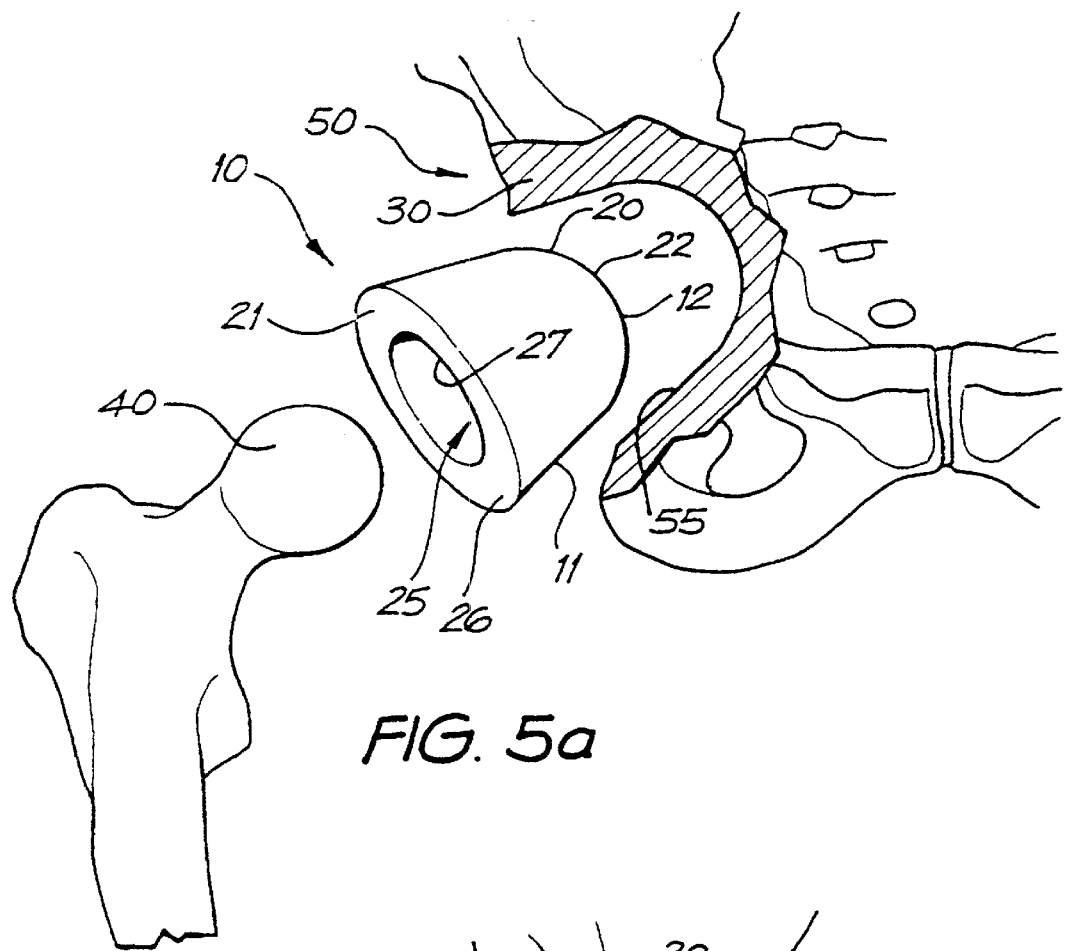
FIG. 5a is an exploded perspective view illustrating the relative positions of the reamed surface of the acetabulum, the socket member according to a preferred embodiment of the invention, and the head of the femur (or prosthesis thereof), as they are each about to be inserted into the right hip.
Figure 5B:
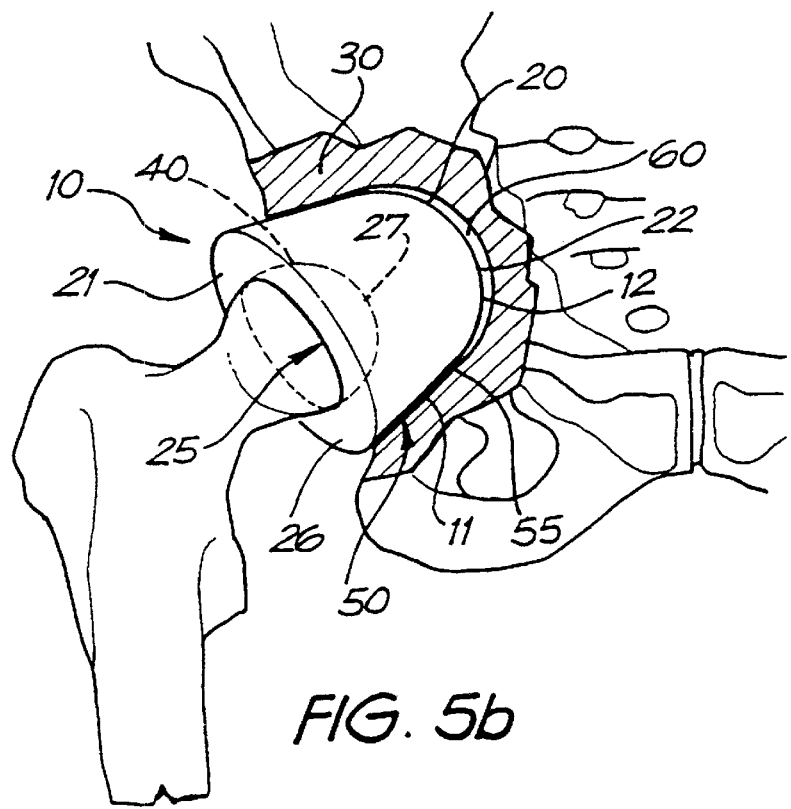
FIG. 5b is a perspective view illustrating the componentry shown in FIG. 5a as correctly inserted into the right hip.

The device according to this invention may be used in a range of arthroplasty procedures, but is of particular applicability to arthroplasty procedures involving the hip joint (see FIG. 1).

The socket member 10 has a bone engaging or contacting surface 20 that is comprised of a first portion which is frusto-conical 11, and a second portion comprising a spherical section 12. Consequently, the foregoing description outlines preferred structural combinations of the frusto-conical portion 11 and portion comprising a spherical section 12 for the bone contacting surface 20 of the socket member 10.

The bone contacting surface 20 of the socket member 10 extends away from the socket member's first surface 21 in such a way that the cross-sectional diameter of the bone contacting surface 20 (in a plane substantially perpendicular to the longitudinal axis) diminishes at one rate for the frusto-conical portion 11, and diminishes at a second different rate for the second portion comprising a spherical section 12 to a rounded extremity 22. In other words, the frusto-conical portion 11 of the bone contacting surface 20 is oriented so that its smallest cross-sectional diameter meets, circumferentially, with the hemispherical section formed by the portion comprising a spherical section 12; and its largest cross-sectional diameter meets, circumferentially, with the first surface 21 of the socket member 10.

As indicated earlier, the scope of this invention is not limited to the embodiments just described. There are multiple variations for the construction of the bone contacting surface 20 having a plurality of portions, each with unique shapes, which fall within its scope. However, as noted in the description of the invention the incorporation of a bone contacting surface 20 having a combination of a frusto-conical portion 11 and portion comprising a spherical section 12 may contribute considerably to the functionality and securability of the socket member 10.

In replacing a socket portion of a joint, the fixation of the socket member 10 must be able to withstand rotational and other movement forces created during articulation of the joint. Having a frusto-conical shape for a portion 11 of the bone contacting surface 20 of the invention is also of particular value, as such a shape has excellent side rotational stabilising capacity.

In addition, such a shape helps to ensure that any compressive forces which the socket member 10 applies to the bone during, for example, weight-bearing, is desirably distributed: with a frusto-conical shape 11, compression of the bone will be greatest at the largest cross-sectional diameter of the frusto-conical portion 11, namely, at around the join with the first surface 21 of the socket member 10. The latter will, when the socket member 10 has been inserted according to this invention, be located near the surface of the bone 30. It is desirable for the greatest compressive force which the socket member 10 applies to the bone 30 to be distributed at this location. This is because, if the greatest compression occurs in deeper regions of the bone 30, for example, those regions adjacent the extremity 22 of the bone contacting surface 20 of the socket member 10, then the surface bone 30 is protected from stress and tends to weaken.

The capacity of a socket member 10 according to this invention to distribute such compressive forces desirably is further augmented by the presence of a portion comprising a spherical section 12 near or at the extremity 22 of the bone contacting surface 20. In preferred embodiments, the bone contacting surface 20 of the socket member 10, despite being comprised of two portions each having unique shapes (11 and 12 respectively), is continuous, in that the meeting loci of these portions 11 and 12 are not interrupted, or constructed, by a sharp edge or a 'step'. When the portion comprising a spherical section 12 is at the extremity 22 of the bone contacting surface 20 it acts as a further means to ensure that no such edge or step is in contact with the surrounding bone 30. The value of ensuring as much, especially near the extremity 22 of the bone contacting surface 20, is that an edge-like or step-like protrusion would, during the application of weight-bearing compressive forces, act as a stress riser on the bone. For the reasons already outlined, among others, this is not desirable.

The bearing surface 25 is located at the first surface 21 of the socket member 10. Such a bearing surface 25, has the capacity to receive the counter-component of a joint such as the head of the femur 40 (or prosthesis thereof) in a hip joint. In fact, the first surface 21 of the of the socket member 10 is comprised of a relatively planar annular surface 26 into which the bearing surface 25 forms an indent.

While there are no particular limitations on the materials to be used in the manufacture of the socket member 10, it is replacing a bony component of a joint, and must, therefore, have similar characteristics in terms of strength and resilience. As already explained, various metals, as well as ceramics, or carbon fibre may all be appropriate. As an integral component of the socket member 10, the bearing surface 25 will also be made of such a material. However, since this surface 25 of the socket member 10 represents the articulating surface of the joint, it is desirable to use a material of high wear resistance such as polyethylene or ceramics. Accordingly, a shell 27 being made of polyethylene, or similar appropriate material, and having a shape which corresponds with the bearing surface 25 is, in the depicted embodiment, machine fitted to the latter. However, although machine fitting provides for a tighter fit and a convenient form of manufacture, it is not a requisite component of this invention that the shell 27 be fitted by machine. Indeed, any appropriate method of fitting the shell 27, including for example, by known methods of clipping it into position, falls within the scope of this invention.

In addition, as the bearing surface 25 comes under load, there may be relative movement, or micro-motion, between the shell 27 and the bearing surface 25 of the socket member 10 to which it is fitted. This can generate wear particles. In order to render less likely such generation, the interface between the bearing surface 25 of the socket member 10 and the shell 27 is surface-coated with a material, such as titanium nitrate or titanium carbide.

Also disclosed is a method for inserting a socket member 10 according to the invention as a prosthetic replacement for the acetabular portion of a hip joint (see FIG. 1). Although not required in many cases, it may initially be necessary for the surgeon to perform a small hemispherical ream into the acetabulum 50. It may be appropriate to do so in cases where this part of the joint has undergone severe pathological degeneration. Nevertheless, whether or not the decision is made to perform the small hemispherical ream, the method generally includes the steps of:

a) bringing a convex surface of a hemispherical cup (not shown) (an appropriate joint determining means for hip joint arthroplasty) into apposition with the exposed surface of the acetabulum 50;

b) manipulating the hemispherical cup (not shown) so that the correct angular orientation for an acetabular portion of a total hip replacement assembly is determined. Such determination is critical, both for ensuring the best alignment and also for finding a position which provides the least likelihood of dislocation. Determination of the correct angular orientation may be achieved by having reference to appropriate anatomical landmarks, by simple visualisation, or with whatever method is preferred by the surgeon;

c) forming a hole (not shown) into the bone 30 adjacent the hemispherical cup (not shown) with a drill bit (not shown), using said hemispherical cup as a guide. The hemispherical cup is normally pre-prepared with a hole designed to receive the drill bit;

d) removing the hemispherical cup (not shown) from apposition with the exposed surface of the acetabulum 50;

e) using the hole drilled in (c) as a guide, reaming an appropriately sized frusto-conical portion of bone from the acetabulum to a desired depth, thereby creating a reamed surface 55 of bone 30. The reamed surface 55 should extend to a depth slightly beyond the depth attained, according to this invention, by the extremity 22 of the bone contacting surface 20 of a fully inserted socket member 10.

f) bringing a socket member 10 according to this invention into contact with the reamed surface 55 of bone 30; and g) securing the socket member 10 to the bone 30. In the depicted embodiment, the socket member 10 is press fit, and not threaded. As explained in (e) above, when the socket member 10 is fully inserted, there should be a small space 60 between the extremity 22 of the bone contacting surface 20 and the reamed surface 55 of bone 30. This space 60 provides room to allow for a small amount of subsidence of the socket member 10 when it is subjected to compressive forces, for example, during weight-bearing.

Reinforced fixation of the socket member 10 in the correct position may additionally be achieved by cement, by a combination of roughening and hydroxyapatite, or by any other appropriate means.

The socket member 10, according to this invention, is now ready to receive the head of the femur 40, or a prosthesis thereof.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A device for use in surgical procedures involving arthroplasty, the device comprising a socket member having a first surface that includes at least a bearing surface adapted to receive a counter component of a joint, and a bone engaging surface, the bone engaging surface having a first surface portion that extends away from a circumferential join with the first surface, a cross-sectional diameter of the first surface portion decreasing at a first rate as the first surface portion extends away from the circumferential join with the first surface, and at least a second surface portion that extends away from a the first surface portion to an extremity, a cross-sectional diameter of the second surface portion decreasing at a second rate, the second rate being different from the first rate, whereby the first surface portion and the second surface portion are arranged relative to each other such that the bone engaging surface is devoid of a step or a corner.

2. The device of claim 1 wherein the bone engaging surface being devoid of a step or a corner prevents the application of undue stress to the surrounding bone.

3. The device of claim 1 when used as a replacement for the acetabular component of a hip joint.

4. The device of claim 1 wherein the first rate of decrease in cross-sectional diameter of the socket member is linear.

5. The device of claim 1 wherein the second rate of decrease in cross-sectional diameter of the socket member is logarithmic or exponential.

6. The device of claim 1 wherein, the second rate of decrease in cross-sectional diameter of the socket member varies as the second surface portion extends away from a line of meeting with the first surface portion and the second surface portion.

7. The device of claim 1 wherein the first surface portion is defined by a frustoconical section of the socket member and the second surface portion is defined by a spherical section of the socket member.

8. The device of claim 7 wherein the frusto-conical section of he socket member is oriented so that its smallest cross-sectional diameter meets, circumferentially, with a hemisphere formed by the spherical section and its largest cross-sectional diameter meets, circumferentially, with the first surface of the socket member.

9. The device of claim 1 wherein the socket member is cotyloidal in configuration with a longitudinal axis.

10. The device of claim 1 wherein the first surface of the socket member comprises a relatively planar surface into which the bearing surface forms an indent.

11. The device of claim 1 wherein the socket member is made from any one of the group comprising metals, ceramics, or carbon fibre.

12. The device of claim 1 wherein the bearing surface of the socket member is made from a material of higher wear resistance relative the remaining material of the socket member.

13. The device of claim 12 wherein the bearing surface is made from polyethylene or a ceramic material.

14. The device of claim 1 wherein a shell of polyethylene having a shape which corresponds with the bearing surface is fitted to the bearing surface.

15. The device of claim 14 wherein an interface formed between the bearing surface of the socket member and the shell is surface-coated with titanium nitrate or titanium carbide.

* * * * *